United States Patent [19]
Jones

[11] Patent Number: 5,223,270
[45] Date of Patent: Jun. 29, 1993

[54] BORIC ACID BASED CLOVE AND SUGAR INSECTICIDE

[76] Inventor: Ivan E. Jones, 61 Horn Church Crescent, Markham, Ontario, Canada, L3R 7C5

[21] Appl. No.: 928,903

[22] Filed: Aug. 12, 1992

[51] Int. Cl.⁵ .................. A01N 25/00; A01N 59/14
[52] U.S. Cl. ........................................ 424/659; 424/84
[58] Field of Search .................................. 424/659, 84

[56] References Cited

U.S. PATENT DOCUMENTS 4,944,950  7/1990  Sakharova ............................ 424/84
4,959,221  9/1990  Holmes ................................ 424/84
4,988,516  1/1991  Herring ................................ 424/84

Primary Examiner—Allen J. Robinson
Attorney, Agent, or Firm—Levisohn, Lerner & Berger

[57] ABSTRACT

An insecticide comprising about 50% to about 90% boric acid, preferably orthoboric acid, and about 1% to about 15% of a sugar preferably, confectionery sugar and about 1% to 15% of cloves, preferably finely ground. The sugar is preferably a powder, about 90% of which will pass through a 200 mesh grid. The insecticide may optionally contain an anticaking agent, corn starch, in the sugar component. The insecticide is used to kill crawling insects such as cockroaches or beetles and is relatively innocuous to humans.

11 Claims, No Drawings

BORIC ACID BASED CLOVE AND SUGAR INSECTICIDE

BACKGROUND OF THE INVENTION

Insects and pests have long been a problem in both dwelling and working place environments. To control such pests and insects, various devices and chemical composition insecticides have been developed. Normally, insecticidal chemical compositions are poisonous and are designed to kill their intended targets. This is accomplished, for example, with compounds that disrupt nerve transmissions within the organisms. Unfortunately, the same poisonous compounds are also toxic to human beings. Consequently, people who are exposed to such compounds can exhibit toxic reactions such as dry mouth, dizziness, incapacitation or even death. The risk of exposure to such compounds is increased when the method of application consists of spraying an aerosol mixture of those compounds. Another problem with such chemicals is that they are generally only effective when directly contacted by the insect and must therefore be used frequently to be truly effective.

Roaches can be difficult to eliminate from the home or place of business. Most of the products sold for roach control require spraying of a room or home and can leave dangerous chemical residues on all surfaces as well as allowing family members and pets to inhale the aerosol.

In an attempt to eliminate the need for frequent dangerous spraying of poisonous compounds, various mechanical means for pest control have also been developed. Frequently, an insect lure is placed in close proximity with a trap which acts to imprison the offending insects. The bait can either be food, or alternatively, a scent which attracts the insect into the trap. The trap itself can be a sticky surface or a containment means which closes upon entry. These so-called bait traps have a limited degree of effectiveness because they only act on the insects which walk into the trap. A small trap will only attract a small number of insects and must frequently be replaced when full. Another problem is the very limited trapping area and consequently the small number of insects which are likely to find their way into such a trap. Additionally, in a dwelling that is highly infested, many such traps must be laid which can lead to an unsightly morass.

Consequently, there exists a need for a relatively safe insect control system. Such a system would not be applied by aerosol in an attempt to avoid widespread inhalation of the insecticide. A relatively safe chemical approach would eliminate the need for many unsightly bait traps. It is also an object of the present invention to have the insect control mechanism be more effective than simple traps. This is accomplished by having the insect coming in contact with the infective composition take the substance back to the nest or "home" where other insects, too, would then come into contact with the insecticide.

DESCRIPTION OF THE PRIOR ART

U.S. Pat. No. 4,959,221 relates to a pest exterminating composition useful for controlling roaches comprising from about 1-75% by weight, of powdered boric acid, from about 1-75% by weight of powdered sugar, and from about 1-50%, by weight, of dried shredded coconut. The coconut, according to the specification of the '221 patent serves as an anticaking agent. It is well known that the boric acid component is the roach killing component whereas the powdered sugar is employed as a roach attractant. The coconut, according to the specification of the '221 patent, serves as an anticaking agent, maintaining the effectiveness of the composition over time. The coconut also serves as an attractant to certain pests.

U.S. Pat. No. 4,617,188 relates to a natural insecticide employing borax and carob. According to the '188 patent, the natural sugar of the carob is not repulsive to the roaches and increases the effectiveness of the the borax as a roach insecticide. The specification also suggests the use of cornstarch as an anticaking agent.

U.S. Pat. No. 4,759,930 relates to an insecticide composition comprising pyrethrum, rotenone or both and one or more of the following: eucalyptus, rosemary, peppermint and boric acid. The composition is used in powder form. According to that patent's specification, the insecticide composition can be present in amounts ranging by volume, from 0% to 90%. The patent does, however, specifically contemplate insecticide compositions where no boric acid is present and is thus quite distinct from the present invention wherein boric acid is necessarily present.

U.S. Pat. No. 3,438,726 relates to boric acid recovery and dehydration. Here, too, there is no suggestion of the use of boric acid, combined with sugar, preferably confectionery sugar, and finely powdered cloves as an insecticide composition.

U.S. Pat. No. 3,514,257 relates to a process for producing metabolic acid by dehydrating orthoboric acid. This patent does not teach the use of orthoboric acid, combined with sugar and cloves, to form an effective insecticide.

U.S. Pat. No. 3,791,435 relates to a continuous dehydration apparatus intended for use in continuous dehydration of wet orthoboric acid to metabolic acid. This patent neither teaches nor suggests the present invention.

U.S. Pat. No. 3,375,198 relates to alkali metal perforates. This patent, too, neither teaches nor suggests the use of boric acid admixed with sugar, confectionery sugar being preferred, and cloves as an insecticide composition.

SUMMARY OF THE INVENTION

An insecticide comprising boric acid, finely powdered cloves and a finely powdered confectionery sugar is disclosed. In a preferred embodiment, orthoboric acid, 80% by weight, is combined with finely powdered confectionery sugar, 10%, by weight, with finely powdered cloves, also 10% by weight. The powdered sugar, preferably sucrose, generally has a particle size capable of substantially passing through a 200 mesh grid. The mixture is to be liberally sprinkled in insect infested areas. The insecticide composition uses no dangerous sprays or bait devices that can allow family members and pets to inhale or come into contact with the chemical insecticide.

The effectiveness of boric acid as an insecticide is well known. See, for example, U.S. Pat. No. 4,617,188. The admixture of sugar to boric acid is known to facilitate attraction of the roaches to the boric acid. The addition of cloves, about 10%, by weight, preferably finely powdered, further enhances the effectiveness of the composition. The cloves provide a strong aromatic scent and attracts many insect types to the boric acid, beyond those present in the immediate vicinity where the product has been sprinkled. Additionally, the powdered confectionery sugar and the finely powdered cloves reduce the tendency of the overall product to cake. Thus, the effectiveness over time of the product is maintained. The use of first, a sweet, the sugar, and secondly, a pleasant aromatic compound, the cloves, effectively camouflages the poisonous bait, the boric acid. The cloves serve as an anticaking agent, too.

The composition disclosed herein offers a safe and effective alternative to sprays and traps. The composition is in crystalline form and placed in areas frequented by roaches going to and from their nests in wall spaces. The roaches will pick up crystals of the material on their feet and carry them back to their nests. During self and cross-grooming, roaches will ingest the particles they collected on their feet while other particles will be dropped in the nest area and picked up by other roaches. Each roach ingesting the boric acid crystals will be killed. The present insecticide destroys roaches that would never be seen or exposed to direct action of insecticide sprays.

DETAILED DESCRIPTION OF THE INVENTION AND THE PREFERRED EMBODIMENT

The insecticide compositions of this invention comprise boric acid in solid powder form, finely ground cloves, and confectionery sugar. The components are blended together to form an even composition powder. Preferably the boric acid is a salt compound with a crystalline formation. Boric acid is present in an amount from about 50% to about 90%; the sugar is present in amounts ranging from about 1% to about 15% by weight and the finely powdered cloves also available in amounts of about 1% to 10%, by weight. The preferred composition comprises 80% boric acid; 10% finely powdered confectionery sugar; and 10%, also by weight, of finely powdered cloves. The preferred form of the boric acid component is orthoboric acid. Since the confectionery sugar has similar tactile characteristics to the boric acid, it is believed that the roaches will ingest the poisonous boric acid because of the "sweetness" of the sugar ingested at the same time.

Any powdered sugar can be used in carrying out this invention. For example, the sugar may be a monosaccharide, a disaccharide or a trisaccharide. Dextrose, sucrose, fructose, lactose, and galactose would all also be suitable.

The size of the particles of sugar can vary from granular, i.e., more than 80% of the grains fit through a 20-100 mesh grid to a fine powder such as fondant wherein 100% of the particles are below 325 mesh. The preferred sugar is sucrose, wherein greater than about 90% of the particles pass through a 200 mesh grid.

Corn starch in an amount of from 1-10%, by weight, but preferably 3-4% of the total sugar content may also be used as an anticaking agent. The anticaking property, whether the cloves, the sugar or the corn starch serves to prevent the powdery composition from sticking or caking together. Thus the effectiveness of the composition is maintained over longer time periods.

The instant composition is especially effective against roach or beetle infestation. Roaches, such as cockroaches, tend to scamper about in corners and crevices and are difficult to eradicate. In operation, the instant composition is sprinkled into crevices and along walls and in other known areas of infestation. The roaches are attracted to the composition by the sugar and aroma of the cloves, and in walking over the composition, boric acid as well as the sugar and cloves contact and adhere to various parts of the cockroach's body.

Roaches are fairly fastidious creatures. They frequently groom and clean all the various parts of their bodies with their mouths. The mouth is used to preen all accessible body parts and the legs are used to groom the remaining parts. The mouth is then used to clean the legs to complete the process. Ingestion of the boric acid crystals during this process will poison the roach and death will result. Roaches are even known to groom and preen one another. In this process, a roach that has contacted the instant composition inadvertently brings both sugar, cloves, and boric acid into the roach's nest. When the roaches clean themselves and each other, they invariably end up consuming some of the poisonous boric acid crystals that have adhered to their bodies. This is toxic to the roach and makes an extremely effective insecticide. The presence of sugar and cloves, together, increases the efficacy of the instant boric acid based insecticide several fold over compositions that do not contain these components. Laboratory studies indicate that a single roach contacting boric acid crystals will carry enough of the crystals back to the nest to kill five to seven other roaches.

The boric acid based compound releases no harmful fumes and leaves no chemical residue.

It appears that the confectionery sugar and powdered clove additives are far more effective as an insecticide additive than ordinary table sugar. Apparently, the insects ingest far more boric acid crystals when it is mixed with the confectionery sugar and cloves than when the boric acid is merely mixed with table sugar. They are more readily attracted to the composition having the cloves than if it were not present. It is believed that the insects can not tactilely or, by odor, detect difference between the boric acid and the confectionery sugar, whereas the conventional table sugar composition, either because of size or smell can be more easily distinguished. Also, it is believed that the roaches ingest the boric acid because of their inability to detect differences in structure (size and shape) between the boric acid and the confectionery sugar. The roaches, upon eating a piece of the sugar find its taste "sweet" and then continues to eat indiscriminately, the sugar and the boric acid. Boric acid, by itself, i.e., not mixed with sugar and cloves is not nearly as effective an insecticide as when the boric acid is mixed with the sugar and cloves. Boric acid mixed with conventional sugar and cloves, however, is not nearly as effective as boric acid mixed with confectionery sugar and cloves.

It should be understood by those skilled in the art that the foregoing specification is not intended to limit the invention to those embodiments described. On the contrary, it is intended to cover all alternatives, modifications and equivalents within the spirit and scope of the inventive concept.

What is claimed is:

1. An insecticide comprising about 50% to about 90% by weight of boric acid, about 1-15%, by weight of cloves and about 1-15% by weight of a sugar.

2. An insecticide according to claim 1 wherein said boric acid substantially comprises orthoboric acid.

3. An insecticide according to claim 1 wherein said sugar is selected from the group consisting of monosaccharides, disaccharides and trisaccharides.

4. An insecticide according to claim 1 wherein greater than about 90% of said sugar comprises a powder capable of passing through a 200 mesh grid.

5. An insecticide according to claim 1 wherein said sugar is selected from the group consisting of dextrose, sucrose, fructose, lactose, and galactose.

6. An insecticide according to claim 1 wherein said boric acid comprises about 80% by weight, said cloves comprise about 10%; and said sugar also comprises about 10% by weight.

7. An insecticide according to claim 1 further comprising an anticaking agent in an amount ranging from about 1% to about 10% by weight of the total amount of said sugar.

8. An insecticide according to claim 7 wherein said anticaking agent comprises cornstarch.

9. An insecticide according to claim 7 wherein said anticaking agent comprises about 3% to about 4% by weight of the total amount of said sugar.

10. An insecticide according to claim 1 wherein said sugar is finely powdered confectionery sugar.

11. An insecticide according to claim 1 wherein said cloves are finely powdered.

* * * * *